US012692240B2

(12) United States Patent
Zheng et al.

(10) Patent No.: US 12,692,240 B2
(45) Date of Patent: Jul. 28, 2026

(54) METHOD FOR PREPARING 3,6-DIAMINOPYRAZINE-2,5-DICARBOXYLIC ACID AND SYNTHETIC INTERMEDIATE THEREOF

(71) Applicants: Hangzhou Zhongmeihuadong Pharmaceutical Co., Ltd., Zhejiang (CN); MediBeacon Inc., St. Louis, MO (US)

(72) Inventors: Junho Zheng, Zhejiang (CN); Xuming Hong, Zhejiang (CN); Duqian Zhang, Zhejiang (CN); Thomas E. Rogers, St. Louis, MO (US); Elena Cacchillo, St. Louis, MO (US)

(73) Assignee: MediBeacon Inc., St. Louis, MO (US)

( * ) Notice: Subject to any disclaimer, the term of this patent is extended or adjusted under 35 U.S.C. 154(b) by 528 days.

(21) Appl. No.: 18/036,108

(22) PCT Filed: Sep. 11, 2021

(86) PCT No.: PCT/CN2021/129540

§ 371 (c)(1),
(2) Date: May 9, 2023

(87) PCT Pub. No.: WO2022/096015

PCT Pub. Date: May 12, 2022

(65) Prior Publication Data

US 2024/0025864 A1 Jan. 25, 2024

Related U.S. Application Data

(60) Provisional application No. 63/111,359, filed on Nov. 9, 2020.

(30) Foreign Application Priority Data

Nov. 27, 2020 (CN) ......................... 202011367514.2

(51) Int. Cl.
*C07D 487/14* (2006.01)
*C07D 241/26* (2006.01)
*C07D 241/28* (2006.01)

(52) U.S. Cl.
CPC ......... *C07D 241/26* (2013.01); *C07D 487/14* (2013.01)

(58) Field of Classification Search
CPC ............................ C07D 487/14; C07D 241/28
See application file for complete search history.

(56) References Cited

FOREIGN PATENT DOCUMENTS

| | | | |
|---|---|---|---|
| CN | 101087767 | A | 12/2007 |
| DE | 102016205615 | A1 | 2/2017 |
| WO | 2006/071759 | A2 | 7/2006 |
| WO | 2022096015 | A1 | 5/2022 |

OTHER PUBLICATIONS

International Search Report and Written Opinion for PCT application No. PCT/CN2021/129540, mailed on Feb. 10, 2022, 18 pages (English translation).
International Preliminary Report on Patentability for PCT application No. PCT/CN2021/129540, mailed on May 8, 2023, 7 pages (English translation).
Baudisch, Oskar, et al., "The Oxidation of 5-Aminouracil," Journal of Biological Chemistry, vol. 71, No. 2, Jan. 1, 1927, pp. 497-499.
Rajagopalan, Raghavan, et al., "Hydrophilic Pyrazine Dyes as Exogenous Fluorescent Tracer Agents for Real-Time Point-of-Care Measurement of Glomerular Filtration Rate," Journal of Medicinal Chemistry, Jun. 13, 2011, vol. 54, pp. 5048-5058.
Taylor, E.C., Jr.; Loux, Harvey M.; Falco, Elvira A.; Hitchings, George H.; "Pyrimidopteridines by Oxidative Self-condensation of Aminopyridines"; Journal of the American Chemical Society, Apr. 20, 1955, vol. 77, pp. 2243-2248.
Extended Search Report for European Application No. 21888707.3 dated Jul. 29, 2024 (10 Pages).

*Primary Examiner* — Bruck Kifle
(74) *Attorney, Agent, or Firm* — Polsinelli PC

(57) ABSTRACT

A method for preparing 3,6-diaminopyrazine-2,5-dicarboxylic acid and a synthetic intermediate thereof. The method comprises the step of preparing pyrimido[4,5-g]pteridine-2,4,7,9(1H,3H,6H,8H)-tetraone or a disalt (pteridine) thereof from 5-aminouracil or a single salt thereof.

38 Claims, No Drawings

METHOD FOR PREPARING 3,6-DIAMINOPYRAZINE-2,5-DICARBOXYLIC ACID AND SYNTHETIC INTERMEDIATE THEREOF

CROSS REFERENCE TO RELATED APPLICATIONS

This application claims the benefit of International Application No. PCT/CN2018/129540, filed Nov. 9, 2021 which claims the benefit of U.S. Provisional Application 63/111, 359, filed Nov. 9, 2020, and CN application Ser. No. 20/201,1367514.2, filed Nov. 27, 2020 the disclosures of which are hereby incorporated by reference in their entirety.

FIELD OF THE INVENTION

The present disclosure relates to a method for preparing 3,6-diaminopyrazine-2,5-dicarboxylic acid and a synthetic intermediate thereof, the method comprising the step of preparing pyrimido[4,5-g]pteridine-2,4,7,9(1H,3H,6H,8H)-tetraone or a disalt (pteridine) thereof from 5-aminouracil or a mono salt thereof.

BACKGROUND OF THE INVENTION 3,6-diaminopyrazine-2,5-dicarboxylic acid (MB-301) is a key intermediate for the preparation of a pyrazine derivative, 2,5-bis[N-(1-carboxyl-2-hydroxy)] carbamoyl-3,6-diaminopyrazine (MB-102) as a fluorescent tracer. In the prior art, there are two synthetic routes for preparing 3,6-diaminopyrazine-2,5-dicarboxylic acid.

Synthetic route 1 (*Dyes and Pigments,* 1998, 39, 49-68) involves the preparation of 2,5-diamino-3,6-dicyanopyrazine from hydrogen cyanide and diphenyl disulfide via cyclization, which is then hydrolysed to give MB-301. The raw material diphenyl disulfide in this route has a foul odor, and hydrogen cyanide is a highly toxic controlled raw material. Therefore, this route has obvious defects and is not suitable for industrial production.

Synthetic route 2 (DE 10 2016 205 615 A1, 2016) uses uracil as a starting material to prepare MB-301 (Formula 4) via nitration, reduction, oxidative cyclization using potassium ferricyanide as an oxidant, and hydrolysis. In the reduction reaction, aqueous ammonia is used as an alkaline reagent and the reaction is conducted at 75° C. Under this condition, aqueous ammonia is volatile, and the ammonia gas produced is harmful to human body. Therefore, the reaction system has potential safety hazards. Another drawback of this synthetic route is that the yield of the oxidative cyclization reaction for preparing pyrimido[4,5-g]pteridine-2,4,7,9(1H,3H,6H,8H)-tetraone of Formula (I') is only 21%, thereby severely limiting the yield of the whole synthetic route, which thus results in low cost efficiency. This synthetic route is not suitable for industrial production.

Synthetic Route 2

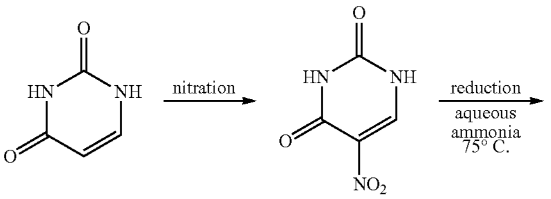

III

-continued

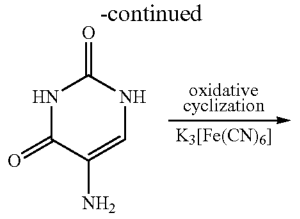

II'

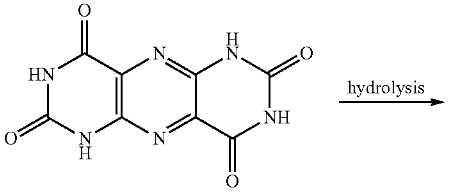

I'
yield = 21%

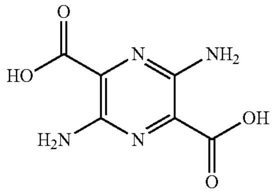

4

Although the first report on the preparation of MB-301 dates back to 1966 (*Dyes and Pigments* 1999, 41, 183-191), serious problems, such as low yield, poor safety, low cost efficiency and unsuitability for industrial production, have not been solved after more than 50 years of development.

Therefore, there is still a need to develop an improved method for the preparation of MB-301 and its synthetic intermediates (in particular, the compound of Formula (I') or a salt thereof), with high yield, high purity, high safety, high cost efficiency, and especially suitability for industrial production. The improved preparation method for the synthetic intermediates (in particular, the compound of Formula (I') or a salt thereof) will translate into higher yield enhancements of MB-301 and consequently yield enhancements and lower unit manufacturing cost of MB-102.

SUMMARY OF THE INVENTION

In one aspect, the present disclosure provides a method for preparing a compound of Formula (I) or a salt thereof (pteridine), Formula (I)

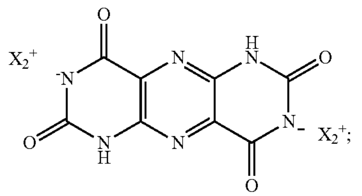

the method comprising simultaneously contacting an aqueous solution of a compound of Formula (II) or a salt thereof:

Formula (II)

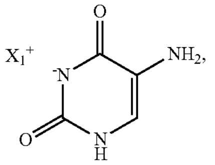

with an aqueous solution comprising a metal oxidant and an aqueous solution comprising a proton acceptor in a vessel to form the compound of Formula (I) or a salt thereof; and wherein $X_1^+$, if present, and $X_2^+$, if present, are independently selected from the group consisting of $H^+$, $Li^+$, $Na^+$, $K^+$, $Rb^+$, $Cs^+$, $NH_4^+$, $Be^{2+}$, $Mg^{2+}$, $Ca^{2+}$, $Sr^{2+}$, and $Ba^{2+}$.

In one aspect, the present disclosure provides a method for preparing pyrimido[4,5-g]pteridine-2,4,7,9(1H,3H,6H,8H)-tetraone of Formula (I'), the method comprising the step of:

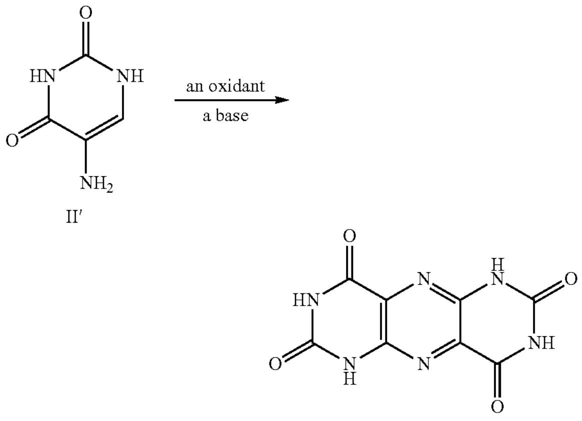

II'

I'

(S2) reacting 5-aminouracil of Formula (II') in the form of a solution A with an oxidant in the form of a solution B in the presence of a base in a reactor to obtain pyrimido[4,5-g]pteridine-2,4,7,9(1H,3H,6H,8H)-tetraone of Formula (I'), wherein the solution A and the solution B are simultaneously added each at a constant flow rate to the reactor, and mixed, and wherein the constant flow rate of the solution A and the constant flow rate of the solution B may be the same or different.

The inventors have found through researches that, by conducting the oxidative cyclization reaction from the compound of Formula (II') to the compound of Formula (I') in the above synthetic route 2 through simultaneously adding the compound of Formula (II') and the oxidant $K_3[Fe(III)(CN)_6]$ each at an appropriate constant flow rate to a reactor for mixing, the yield of the compound of Formula (I') and the overall yield of the whole synthetic route, and improve the cost effectiveness can be greatly improved.

In addition, the inventors also changed the base used in the reduction reaction of the above synthetic route 2 to replace aqueous ammonia, which made the synthetic process safer and more environmentally friendly. Based on the above researches and findings, the inventors have completed the present invention.

The above and other aspects of the present disclosure are described in more detail below.

DETAILED DESCRIPTION OF THE INVENTION

In a first aspect, provided herein are methods for preparing Pteridine, a key intermediate in the preparation of MB-301, in high yield and high purity. Advantageously, it was discovered that simultaneous addition of the reactants increases the yield to about 90%, which is a significant increase over the prior art methods. The methods disclosed herein include other process improvements, such as the temperature at which the method is conducted, the optimal molar ratio of the starting materials, the rate of addition of the starting materials, the concentrations of starting materials, and the rapid rate at which the reaction takes place at common reaction temperatures.

I. Method for Preparing Compound of Formula (I)

The present disclosure encompasses a method for preparing a compound of Formula (I) or a salt thereof, Formula (I)

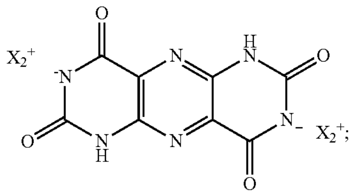

the method comprising simultaneously contacting an aqueous solution of a compound of Formula (II) or a salt thereof:

Formula (II)

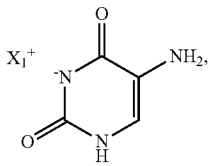

with an aqueous solution comprising a metal oxidant and an aqueous solution comprising a proton acceptor in a vessel to form the compound of Formula (I) or a salt thereof; and wherein $X_1^+$, if present, and $X_2^+$, if present, are independently selected from the group consisting of $H^+$, $Li^+$, $Na^+$, $K^+$, $Rb^+$, $Cs^+$, $NH_4^+$, $Be^{2+}$, $Mg^{2+}$, $Ca^{2+}$, $Sr^{2+}$, and $Ba^{2+}$. Each of the starting materials is described below in more detail.

(a) Aqueous Solution of a Compound of Formula (II)

The compound of Formula (II) is detailed above. In some embodiments, $X_1^+$ may be hydrogen. In other embodiments, $X_1^+$ may be a monovalent cation selected from $Li^+$, $Na^+$, $K^+$, $Rb^+$, $Cs^+$, or $NH_4^+$. In still other embodiments, $X_1^+$ may be a divalent cation selected from $Be^{2+}$, $Mg^{2+}$, $Ca^{2+}$, $Sr^{2+}$, or $Ba^{2+}$. In preferred embodiments, $X_1^+$ is a monovalent cation selected from $Na^+$, $K^+$, or $NH_4^+$.

The water used to prepare the aqueous solution of the compound of Formula (II) may be deionized water, distilled water, distilled deionized water, or potable (tap) water.

The aqueous solution of the compound of Formula (II) may be prepared using various methods. In one embodiment, the compound of Formula (II) wherein $X_1^+$ is a monovalent cation or a divalent cation may be dissolved in water until homogeneity is achieved. In another embodiment, the compound of Formula (II) wherein $X_1^+$ is $H^+$ may be suspended in water and an equal molar amount of a proton acceptor may be added, thereby forming the salt of Formula (II).

In general, the aqueous solution of the compound of Formula (II) may have a concentration ranging from about 0.75M to about 1.25M. In various embodiments, the aqueous solution of the compound of Formula (II) may have a concentration ranging from about 0.75M to about 1.25M, from about 0.8M to about 1.0M, or from about 0.85M to about 0.95M. In one preferred embodiment, the concentration of the aqueous solution of the compound of Formula (II) may be about 0.9M.

(b) Aqueous Solution of a Metal Oxidant

The aqueous solution of the metal oxidant is prepared by dissolving the appropriate metal oxidant in water until a homogeneous solution is achieved.

A variety of metal oxidants may be used in this method. Generally the metal oxidant comprises Fe(III) or Mn(III). Non-limiting examples of useful metal oxidants comprising Fe(III) or Mn(III) may be potassium ferricyanide, lithium ferricyanide, sodium ferricyanide, ferric chloride, ferric bromide, manganese (III) acetylacetonate, and manganese (III) acetate. In one preferred embodiment, the metal oxidant may be potassium ferricyanide.

In some embodiments, the metal oxidant may also be sodium pentacyano-monocarbonylferroate ($Na_2[Fe(CN)_5(CO)]$), or sodium pentacyanoammineferroate ($Na_3[Fe(CN)_5 NH_3]$).

The water used to prepare the aqueous solution of the metal oxidant may be deionized water, distilled water, distilled deionized water, or potable (tap) water.

Generally, the aqueous solution of a metal oxidant comprising Fe(III) or Mn(III) may have a concentration ranging from about 0.75M to about 1.25M. In various embodiments, the aqueous solution of the metal oxidant comprising Fe(III) or Mn(III) may have a concentration ranging from about 0.75M to about 1.25M, from about 0.8M to about 1.0M, or from about 0.85M to about 0.95M. In one preferred embodiment, the metal oxidant comprising Fe(III) or Mn(III) may have a concentration of about 0.9M.

In general, the molar ratio of the metal oxidant to the compound of Formula (II) may range from about 2.8:1.0 to about 3.5:1.0. In various embodiments, the molar ratio of the metal oxidant to the compound of Formula (II) may range from about 2.8:1.0 to about 3.5:1.0, from about 2.9:1.0 to about 3.3:1.0, or from about 3.0:1.0 to about 3.2:1.0. In one preferred embodiment, the molar ratio of the metal oxidant to the compound of Formula (II) may range from about 3.0:1.0 to about 3.2:1.0.

(c) Aqueous Solution of the Proton Acceptor

The aqueous solution of the proton acceptor may be prepared by dissolving the appropriate proton acceptor in the appropriate amount of water until the desired concentration is achieved or adding the appropriate amount of water to a commercial concentrated solution of the proton acceptor.

A variety of proton acceptors may be used in the process. Non-limiting examples of suitable proton acceptors may be selected from the group consisting of $Li_2CO_3$, LiOH, $Na_2CO_3$, NaOH, $K_2CO_3$, KOH, $Rb_2CO_3$, RbOH, $Cs_2CO_3$, CsOH, $NH_4OH$, $BeCO_3$, $Be(OH)_2$, $MgCO_3$, $Mg(OH)_2$, $CaCO_3$, $Ca(OH)_2$, $SrCO_3$, $Sr(OH)_2$, $BaCO_3$, or $Ba(OH)_2$. In some embodiments, the proton acceptor may be $Li_2CO_3$, LiOH, $Na_2CO_3$, NaOH, $K_2CO_3$, KOH, $Rb_2CO_3$, RbOH, $Cs_2CO_3$, CsOH, or $NH_4OH$. In a preferred embodiment, the proton acceptor is $Na_2CO_3$, NaOH, $K_2CO_3$, KOH, $NaHCO_3$, $(CH_3)_4NOH$, or $NH_4OH$.

The water used to prepare the aqueous solution of the proton acceptor may be deionized water, distilled water, distilled deionized water, or potable (tap) water.

Generally, the aqueous solution of the proton acceptor may have a concentration ranging from about 0.75M to about 1.50M. In various embodiments, the aqueous solution of the proton acceptor may have a concentration ranging from about 0.75M to about 1.50M, from about 0.8M to about 1.4M, or from about 0.90M to about 1.35M. In one preferred embodiment, the concentration of the proton acceptor may have a concentration ranging from 0.90M to about 1.35M.

In general, the molar ratio of the proton acceptor to the compound of Formula (II) may range from about 3.5:1.0 to about 6.0:1.0. In various embodiments, the molar ratio of the proton acceptor to the compound of Formula (II) may range from about 3.5:1.0 to about 6.0:1.0, from about 3.8:1.0 to about 5.5:1.0, or from about 4.0:1.0 to about 4.2:1.0. In one preferred embodiment, the molar ratio of the proton acceptor to the compound of Formula (II) may range from about 4.0:1.0 to about 4.2:1.0.

(d) Reaction Conditions

The method comprises simultaneously contacting the aqueous solution of the compound of Formula (II), the aqueous solution of the metal oxidants and the aqueous solution of the proton acceptor. For example, the aqueous solution of the compound of Formula (II) and the aqueous solution of the metal oxidant may be simultaneously added (e.g., via injection) to a vessel containing the aqueous solution of the proton acceptor. Those skilled in the art can readily envision alternate addition strategies in which the three solutions are contacted simultaneously.

The aqueous solution of the compound of Formula (II) and the aqueous solution of the metal oxidant may be simultaneously added each at a constant rate to the vessel, and mixed. The respective constant rates of the two aqueous solutions may be the same or different. In some embodiments, the ratio of the rate of the aqueous solution of the compound of Formula (II) to the rate of the aqueous solution of the metal oxidant may range from about 1:10 to 1:1, including from about 1:8 to 1:1.5, from about 1:6 to 1:2, or from about 1:4 to 1:3. The two aqueous solutions may be simultaneously added, each through a constant flow control equipment, such as a peristaltic pump or a syringe pump, to the vessel.

In some embodiments, the rate of the aqueous solution of the compound of Formula (II) and the rate of the aqueous solution of the metal oxidant are each not more than about 1000 mL/min, for example, not more than about 900 mL/min, about 800 mL/min, about 700 mL/min, about 600 mL/min, about 500 mL/min, about 400 mL/min, about 300 mL/min, about 200 mL/min, or about 100 mL/min, or not more than about 90 mL/min, about 80 mL/min, about 60 mL/min, about 50 mL/min, or about 30 mL/min, for example, not more than about 25 mL/min, not more than about mL/min, or not more than about 15 mL/min, for example, from about 2 to 30 mL/min, from about 4 to 25 mL/min, from about 8 to 20 mL/min, or from about 10 to mL/min.

In some embodiments, the proton acceptor and the compound of Formula (II) may be comprised together in the same aqueous solution.

In some embodiments, the vessel may be a microreactor, such as a microchannel reactor or a micromixer. In some embodiments, the vessel may be an ordinary reactor, such as a tubular reactor or a tank reactor.

The method, as described herein, may be conducted in a batch mode, semi-continuous mode, or continuous mode.

In general, the reaction will be conducted at a temperature that ranges from about −6° C. to about 25° C. In various embodiments, the temperature of the reaction may range from about −6° C. to about 25° C., from about −6° C. to about 10° C., or from about −6° C. to about 0° C. In one embodiment, the reaction may be conducted at a temperature of about 0° C. The reaction typically is performed under ambient pressure. The reaction may also be conducted under an inert atmosphere, for example, under nitrogen, argon or helium.

Generally, the reaction is deemed complete within seconds after the simultaneous and complete addition of the aqueous solution of Formula (II), the aqueous solution of the metal oxidant, and the aqueous solution of the proton acceptor are completely added. The completion time for the reaction indicates the rapid rate of reaction.

In this context, a "reaction is deemed complete" generally means that the reaction mixture contains a significantly diminished amount of the compound of Formula (II). Typically, the amount of the compound of Formula (II) remaining in the reaction mixture at the end of the reaction may be less than about 1.0%, less than about 0.5%, or less than about 0.1%.

For example, the compound of Formula (I) may be isolated by various methods known in the art, such as filtration or centrifugation. The compound of Formula (I) may further be washed with a minimal amount of water and dried using various methods known in the art.

The compound of Formula (I) may have a yield of at least about 70%. In various embodiments, the compound of Formula (I) may have a yield of at least about 75%, at least about 80%, at least about 85%, at least about 90%, at least about 92.5%, or at least about 95%. In specific embodiments, the yield may be at least about 90%.

In general, the yield of the compound of Formula (I) prepared by the method disclosed herein is significantly higher than the yield of said compound prepared by prior art methods.

The compound of Formula (I) may have a purity greater than about 95% as measured by high-performance liquid chromatography (HPLC) or other methods known in the art. In various embodiments, the compound of Formula (I) may have a purity greater than about 95%, greater than about 97%, or greater than about 98% as measured by HPLC. In one preferred embodiment, the compound of Formula (I) has a purity greater than 98% as measured by HPLC.

(e) Exemplary Embodiments

In some embodiments, the proton acceptor is selected from the group consisting of $Na_2CO_3$, NaOH, $K_2CO_3$, KOH, $NaHCO_3$, $(CH_3)_4NOH$, or $NH_4OH$; the metal oxidant is selected from the group consisting of potassium ferricyanide, lithium ferricyanide, sodium ferricyanide, ferric chloride, ferric bromide, manganese (III) acetylacetonate, or manganese (III) acetate; the molar ratio of the proton acceptor to the compound of Formula (II) ranges from about 3.5:1.0 to about 6.0:1.0; the molar ratio of the metal oxidant to the compound of Formula (II) ranges from about 2.8:1.0 to about 3.5:1.0; and the method is conducted at a temperature ranging from about −6° C. to about 25° C. The compound of Formula (I) is formed within seconds of the simultaneous contacting of the aqueous solutions of the compound of Formula (II), proton acceptor, and metal oxidant. The compound of Formula (I) has a percent yield of at least 90%, or at least 95%, and a purity of at least 98%.

In another embodiment, the proton acceptor is selected from the group consisting of $Na_2CO_3$, NaOH, $K_2CO_3$, KOH, $NaHCO_3$, $(CH_3)_4NOH$, or $NH_4OH$; the metal oxidant is selected from the group consisting of potassium ferricyanide, lithium ferricyanide, sodium ferricyanide, ferric chloride, ferric bromide, manganese (III) acetylacetonate, or manganese (III) acetate; the molar ratio of the proton acceptor to the compound of Formula (II) ranges from about 4.0:1.0 to about 4.2:1.0; the molar ratio of the metal oxidant to the compound of Formula (II) ranges about 3.0:1.0 to about 3.2:1.0; and the method is conducted at a temperature ranging from −6° C. to about 0° C. The compound of Formula (I) is formed within seconds of the simultaneous contacting of the aqueous solutions of the compound of Formula (II), proton acceptor, and metal oxidant. The compound of Formula (I) has a percent yield of at least 90%, or at least 95%, and a purity of at least 98%.

In certain embodiments, the proton acceptor is KOH; the metal oxidant is potassium ferricyanide; the molar ratio of KOH to the compound of Formula (II) ranges from about 3.5:1.0 to about 6.0:1.0; the molar ratio of potassium ferricyanide to the compound of Formula (II) ranges from about 2.8:1.0 to about 3.5:1.0; and the method is conducted at a temperature ranging from about −6° C. to about 25° C. The compound of Formula (I) is formed within seconds of the simultaneous contacting of the aqueous solutions of the compound of Formula (II), proton acceptor, and metal oxidant. The compound of Formula (I) has a percent yield of at least 90%, or at least 95%, and a purity of at least 98%.

In particular embodiments, the proton acceptor is KOH; the metal oxidant is potassium ferricyanide; the molar ratio of KOH to the compound of Formula (II) ranges from about 4.0:1.0 to about 4.2:1.0; the molar ratio of potassium ferricyanide to the compound of Formula (II) ranges from about 3.0:1.0 to about 3.2:1.0; and the method is conducted at a temperature ranging from about −6° C. to about 0° C. The compound of Formula (I) is formed within seconds of the simultaneous contacting of the aqueous solutions of the compound of Formula (II), proton acceptor, and metal oxidant. The compound of Formula (I) has a percent yield of at least 90%, or at least 95%, and a purity of at least 98%.

In a second aspect, the present disclosure provides a method for preparing pyrimido[4,5-g]pteridine-2,4,7,9(1H,3H,6H,8H)-tetraone of Formula (I'), the method comprising the step of:

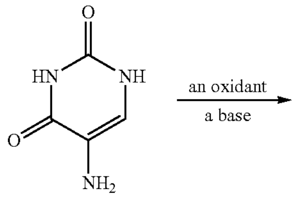

II'

-continued

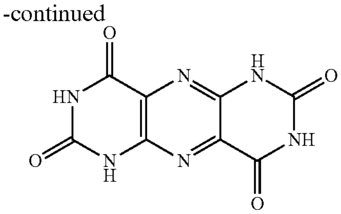

I'

(S2) reacting 5-aminouracil of Formula (II') in the form of a solution A with an oxidant in the form of a solution B in the presence of a base in a reactor to obtain pyrimido[4,5-g]pteridine-2,4,7,9(1H,3H,6H,8H)-tetraone of Formula (I'), wherein the solution A and the solution B are simultaneously added each at a constant flow rate to the reactor, and mixed, and wherein the constant flow rate of the solution A and the constant flow rate of the solution B may be the same or different.

In some embodiments, the base may be added as a separate solution to the reactor. Alternatively, in other embodiments, the base is added to the reactor with its presence in only one of the solution A and the solution B. In some embodiments, the base is comprised in the solution A together with the 5-aminouracil; and in other embodiments, the base is comprised in the solution B together with the oxidant. The present disclosure also encompasses embodiments in which a portion of the base is comprised in the solution A together with the 5-aminouracil and the other portion is comprised in the solution B together with the oxidant. In a preferred embodiment, the base is added to the reactor with it being comprised only in the solution A together with the 5-aminouracil.

In the reaction mixture obtained in the oxidative cyclization step of Synthetic route 2, the inventors detected the presence of urea which is a by-product of the oxidative cyclization reaction. Without hoping to be bound by any theory, the inventors speculate that a transient intermediate is produced during the reaction that undergoes severe degradation (to produce urea), which may be the main reason for the low yield of this reaction step. By simultaneously adding the two solutions each at an appropriate constant flow rate to the reactor for mixing by using, for example, microfluidic technology (including, for example, precisely controlling the feed amounts and the mixing degree of the reactants), however, the method according to the present disclosure can avoid or reduce the degradation of the transient intermediate and thereby greatly improve the yield of the compound of Formula (I') which may be as high as 40% or more, preferably 50% or more, more preferably 60% or more, even more preferably 80% or more (e.g., about 84%).

In some embodiments, the solution A and the solution B may be simultaneously added, each through a constant flow control equipment, such as a peristaltic pump or a syringe pump, to the reactor.

In some embodiments, the flow rate of the solution A and the flow rate of the solution B are each not more than about 1000 mL/min, for example, not more than about 900 mL/min, about 800 mL/min, about 700 mL/min, about 600 mL/min, about 500 mL/min, about 400 mL/min, about 300 mL/min, about 200 mL/min, or about 100 mL/min, or not more than about 90 mL/min, about 80 mL/min, about 60 mL/min, about 50 mL/min, or about 30 mL/min, for example, not more than about 25 mL/min, or not more than about 20 mL/min, for example, from about 2 to 30 mL/min, from about 4 to 25 mL/min, from about 8 to 20 mL/min, or from about 10 to 15 mL/min. Advantageously, the flow rate of the solution A and the flow rate of the solution B are each not more than about 15 mL/min. In some embodiments, the flow rate of the solution A and the flow rate of the solution B each range from about 2 to 15 mL/min, for example, from about 3 to 12 mL/min, or from about 6 to 10 mL/min. In some preferred embodiments, the flow rate of the solution A is from about 2 to 10 mL/min, such as about 2, 3, 4, 5, 6, 7, 8, 9 or 10 mL/min. In some preferred embodiments, the flow rate of the solution B is from about 2 to 15 mL/min, such as about 2, 3, 4, 6, 8, 12, 14 or 15 mL/min.

The flow rate of the solution A and the flow rate of the solution B may be the same or different. Advantageously, the flow rate of the solution A is less than or equal to the flow rate of the solution B. In some embodiments, the ratio of the flow rate of the solution A to the flow rate of the solution B ranges from about 1:10 to 1:1, including about 1:1, or from about 1:10 to less than 1:1, for example, from about 1:8 to 1:1.5, from about 1:6 to 1:2, or from about 1:4 to 1:3, and preferably from about 1:3 to 1:1. In some preferred embodiments, the ratio of the flow rate of the solution A to the flow rate of the solution B is about 1:2 or about 1:3 (e.g., about 2 and 6 mL/min, respectively). Particularly advantageously, the inventors found that the simultaneous addition of the two solutions to the reactor at the same constant flow rate offers the compound of Formula (I') in a higher yield. Thus, in a particularly preferred embodiment, the ratio of the flow rate of the solution A to the flow rate of the solution B is about 1:1, for example, both are about 2, 3, 6 or 10 mL/min.

In some embodiments, the molar ratio of the base to the 5-aminouracil of Formula (II') ranges from about 3.0:1.0 to about 6.0:1.0. In some preferred embodiments, the molar ratio of the base to the compound of Formula (II') ranges from about 3.0:1.0 to about 5.5:1.0.

In some embodiments, the molar ratio of the oxidant to the 5-aminouracil of Formula (II') ranges from about 3.0:1.0 to about 3.5:1.0. In some preferred embodiments, the molar ratio of the metal oxidant to the compound of Formula (II') ranges from about 3.0:1.0 to about 3.4:1.0.

In some embodiments, the solvent in the solution A and the solvent in the solution B are each a polar solvent, preferably one, two or more selected from the group consisting of water, methanol, ethanol, acetonitrile and tetrahydrofuran, more preferably water.

In some embodiments, the solution A and the solution B each have a temperature ranging from about 0 to 8° C., for example, from about 0 to 4° C., or from about 2 to 6° C.

In some embodiments, the reaction in step S2 is conducted at a temperature of from about −20 to 20° C., preferably from about −10 to 10° C., for example, from about −5 to 5° C., such as about −10, −5, 0 or 5° C.

In some embodiments, the oxidant is used in about 3 to 5 equivalents, relative to the 5-aminouracil of Formula (II').

In some embodiments, the oxidant is a reagent comprising iron(III), preferably one or more selected from the group consisting of potassium ferricyanide ($K_3[Fe(III)(CN)_6]$), sodium pentacyano-monocarbonylferroate ($Na_2[Fe(CN)_5(CO)]$) and sodium pentacyanoammineferroate ($Na_3[Fe(CN)_5NH_3]$), preferably potassium ferricyanide. In some embodiments, the oxidant may also be one or more selected from the group consisting of lithium ferricyanide, sodium ferricyanide, ferric chloride, and ferric bromide. In other embodiments, the oxidant may also be a reagent comprising Mn(III), such as manganese (III) acetylacetonate and manganese (III) acetate.

In some embodiments, the base in step S2 is one or more selected from the group consisting of sodium hydroxide, sodium bicarbonate, sodium carbonate, potassium hydroxide, potassium bicarbonate, potassium carbonate, lithium hydroxide and aqueous ammonia, preferably potassium hydroxide. In some embodiments, the base may also be one or more selected from the group consisting of $Li_2CO_3$, $Rb_2CO_3$, RbOH, $Cs_2CO_3$, CsOH, $BeCO_3$, $Be(OH)_2$, $MgCO_3$, $Mg(OH)_2$, $CaCO_3$, $Ca(OH)_2$, $SrCO_3$, $Sr(OH)_2$, $BaCO_3$ and $Ba(OH)_2$.

There is no specific limitation on the amount of the base in step S2, as long as the reaction can be conducted. In some embodiments, the base is used in about 3 to 5 equivalents, relative to the 5-aminouracil of Formula (II').

The reaction may be conducted for any suitable period of time, such as a period of from about 10 seconds to 10 minutes or more, for example, from about 20 seconds to 8 minutes, from about 30 seconds to 6 minutes, from about 40 seconds to 5 minutes, or from about 50 seconds to 4 minutes.

Examples of the reactor include, but are not limited to, microreactors and ordinary reactors.

In some preferred embodiments, the reactor is a microreactor, such as a microchannel reactor or a micromixer. In a further preferred embodiment, the method for preparing pyrimido[4,5-g]pteridine-2,4,7,9(1H,3H,6H,8H)-tetraone of Formula (I') of the present disclosure comprises the step of:

(S2) simultaneously adding a solution of 5-aminouracil of Formula (II') and sodium hydroxide or potassium hydroxide, preferably potassium hydroxide, in water at about 0 to 4° C. and an aqueous solution of potassium ferricyanide at about 0 to 4° C. at the same constant flow rate to a microreactor for mixing, and reacting at a temperature ranging from about −5 to 5° C. to obtain pyrimido[4, 5-g]pteridine-2,4,7,9(1H,3H,6H,8H)-tetraone of Formula (I'), wherein the constant flow rate preferably ranges from about 3 to 10 mL/min.

In other preferred embodiments, the reactor is an ordinary reactor, such as a tubular reactor or a tank reactor. Preferably, the reactor has been pre-cooled to a temperature ranging from about 0° C. to −20° C., for example, from about −5° C. to −15° C., or from about −10° C. to −15° C. Preferably, when stirring is allowed, the solution A and the solution B are mixed by stirring at a speed ranging from, for example, about 100 to 1000 rpm (for example, from about 200 to 900 rpm, from about 300 to 800 rpm, from about 400 to 700 rpm, or from about 500 to 600 rpm). According to such embodiments, the method for preparing pyrimido[4,5-g]pteridine-2,4,7,9(1H,3H,6H, 8H)-tetraone of Formula (I') of the present disclosure comprises the step of:

(S2) under stirring at a speed ranging from about 200 to 600 rpm (for example, from about 300 to 500 rpm), simultaneously adding a solution of 5-aminouracil of Formula (II') and sodium hydroxide or potassium hydroxide, preferably potassium hydroxide, in water at about 0 to 4° C. and an aqueous solution of potassium ferricyanide at about 0 to 4° C., each at a constant flow rate, to the reactor precooled to a temperature ranging from about 0° C. to about −20° C., for example, at about −10° C., for mixing, to obtain pyrimido[4,5-g]pteridine-2,4,7,9(1H,3H,6H,8H)-tetraone of Formula (I'), wherein the flow rate ratio of the solution of 5-aminouracil to the solution of potassium ferricyanide is about 1:2.

In some embodiments, the method further comprises the following work-up operations: filtering the reaction mixture of step S2, washing the solid product obtained by filtration (e.g., with water or 1 N hydrochloric acid), and drying the solid product.

In a third aspect, the present disclosure provides a method for preparing 3,6-diaminopyrazine-2,5-dicarboxylic acid of Formula 4, the method comprising the steps of:

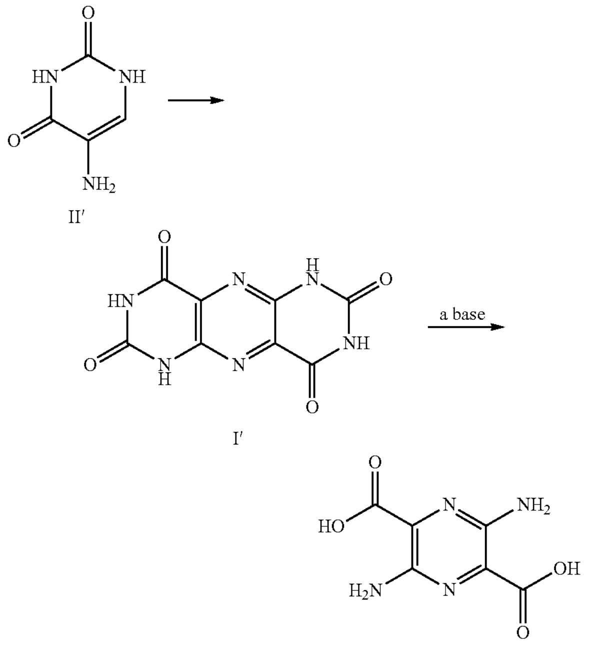

II'

I'

4

(S2') preparing pyrimido[4,5-g]pteridine-2,4,7,9(1H,3H, 6H,8H)-tetraone of Formula (I') from 5-aminouracil of Formula (II') by the method according to the second aspect of the present disclosure above; and (S3) hydrolyzing the pyrimido[4,5-g]pteridine-2,4,7,9(1H,3H,6H,8H)-tetraone of Formula (I') in the presence of a base to obtain 3,6-diaminopyrazine-2,5-dicarboxylic acid of Formula 4.

In some embodiments, the hydrolysis in step S3 is conducted in a polar solvent. In some embodiments, the polar solvent is one or more selected from the group consisting of water, methanol, ethanol, acetonitrile, tetrahydrofuran, diethylene glycol dimethyl ether and methyl isobutyl ketone, and preferably water.

In some embodiments, the base in step S3 is one or more selected from the group consisting of sodium hydroxide, sodium bicarbonate, sodium carbonate, potassium hydroxide, potassium bicarbonate, potassium carbonate and lithium hydroxide, and preferably sodium hydroxide.

In some embodiments, the hydrolysis in step S3 is conducted at a temperature ranging from about 150 to 200° C., and preferably from about 170 to 180° C.

The hydrolysis may be conducted for a suitable period of time, for example, about 4 to 8 hours.

In some embodiments, the method further comprises the following work-up operations: filtering the reaction mixture of step S3, washing the solid product obtained by filtration (e.g., with water or 1 N hydrochloric acid), and drying the solid product.

In some embodiments, the methods according to the second and third aspects of the present disclosure above may each further comprise the step of:

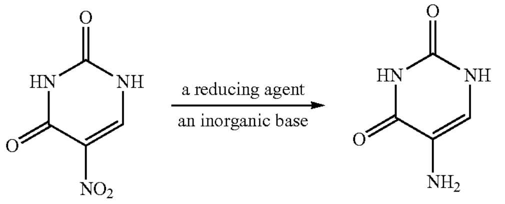

III II'

(S1) reacting 5-nitrouracil of Formula (III) with a reducing agent in the presence of an inorganic base to obtain 5-aminouracil of formula (II'), wherein the inorganic base is not ammonia.

The reaction in step S1 may be conducted in a suitable solvent, such as water. For example, the reaction may be conducted by adding the reducing agent in batches to an aqueous solution containing the 5-nitrouracil of Formula (III) and the inorganic base.

In some embodiments, in step S1, the reducing agent is used in about 1 to 6 equivalents, relative to the 5-nitrouracil of Formula (III).

In some embodiments, in step S1, the reducing agent is used in about 4 to 6 equivalents, relative to the 5-nitrouracil of Formula (III).

In some embodiments, the inorganic base is one or more selected from the group consisting of sodium hydroxide, potassium hydroxide, lithium hydroxide, sodium carbonate, potassium carbonate, sodium bicarbonate and potassium bicarbonate, and preferably sodium bicarbonate.

There is no specific limitation on the amount of the base in step S1, as long as the reaction can be conducted. In some embodiments, in step S1, the inorganic base is used in about 2 to 9 equivalents, relative to the 5-nitrouracil of Formula (III).

In some embodiments, the reducing agent is one or more selected from the group consisting of $Na_2S_2O_4$, hydrogen, iron powder, and zinc powder, and preferably $Na_2S_2O_4$.

In some embodiments, the reaction temperature in step S1 ranges from about 60 to 90° C., preferably from about 70 to 85° C., more preferably from about 75 to 85° C., for example, from about 75 to 80° C., or from about 80 to 85° C.

In some embodiments, the reaction time in step S1 is from about 1 to 10 hours, for example, from about 2 to 8 hours, preferably from about 3 to 6 hours, such as about 3, 4, 5 or 6 hours.

In some embodiments, the method further comprises the following work-up operations: filtering the reaction mixture of step S1, washing the solid product obtained by filtration (e.g., with water), and drying the solid product.

Surprisingly, in addition to increasing the safety of the production process and reducing the potential pollution of the environment, the yield of the compound of Formula (II') is significantly increased, for example, up to 92% (Example 11, as compared to a yield of 65% for Synthetic route 2 (see Comparative Example 1)), by changing the inorganic base in step S1 to avoid the use of aqueous ammonia.

In a fourth aspect, the present disclosure provides a method for preparing 5-aminouracil of Formula (II'), the method comprising the step of:

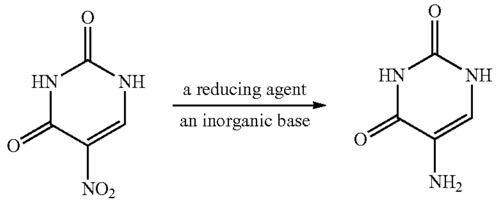

III II'

(S1) reacting 5-nitrouracil of Formula (III) with a reducing agent in the presence of an inorganic base to obtain 5-aminouracil of Formula (II'), wherein the inorganic base is not ammonia.

Some embodiments according to this aspect are as described above.

Definitions

When introducing elements of the embodiments described herein, the articles “a”, “an”, “the” and “said” are intended to mean that there are one or more of the elements. The terms “comprising”, “including” and “having” are intended to be inclusive and mean that there may be additional elements other than the listed elements.

The term “about”, particularly in reference to a given quantity, is meant to encompass a deviation of ±10%, preferably ±5%, and more preferably ±2%.

As used herein, the term “include”, “comprise”, “have”, “contain”, or “involve”, as well as other variants thereof, is inclusive or open-ended and does not exclude other unlisted elements or method steps, even though said other unlisted elements or method steps are not necessarily present (i.e., these terms also encompass the term “consist essentially of . . . ” and “consist of . . . ”).

As various changes could be made in the above-described methods without departing from the scope of the invention, it is intended that all matter contained in the above description and in the examples given below, shall be interpreted as illustrative and not in a limiting sense.

This disclosure encompasses the following embodiments and combinations of any two or more of them, unless such combinations are mutually contradictory or infeasible.

Embodiment 1. A method for preparing pyrimido[4,5-g]pteridine-2,4,7,9(1H,3H, 6H,8H)-tetraone of Formula (I'), wherein the method comprises the step of:

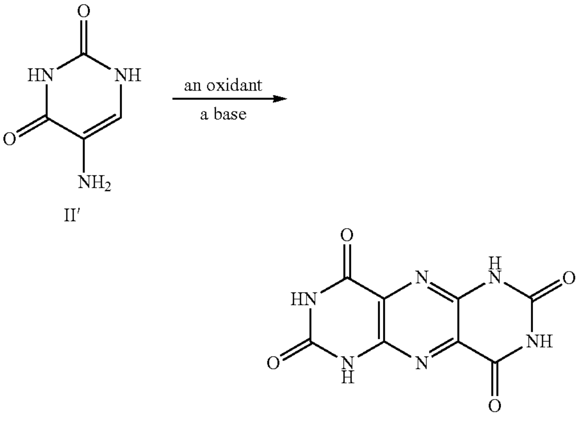

II' I'

(S2) reacting 5-aminouracil of Formula (II') in the form of a solution A with an oxidant in the form of a solution B in the presence of a base in a reactor to obtain pyrimido[4,5-g]pteridine-2,4,7,9(1H,3H,6H,8H)-tetraone of Formula (I'), wherein the solution A and the solution B are simultaneously added each at a constant flow rate to the reactor, and mixed, and wherein the constant flow rate of the solution A and the constant flow rate of the solution B may be the same or different.

Embodiment 2. The method of embodiment 1, wherein the base is added to the reactor with its presence in only one of the solution A and the solution B.

Embodiment 3. The method of embodiment 1 or 2, wherein the base is comprised only in the solution A together with the 5-aminouracil.

Embodiment 4. The method of embodiment 1 or 2, wherein the base is comprised only in the solution B together with the oxidant.

Embodiment 5. The method of embodiment 1 or 2, wherein a portion of the base is comprised in the solution A together with the 5-aminouracil, and the other portion is comprised in the solution B together with the oxidant.

Embodiment 6. The method of any one of embodiments 1 to 5, wherein the solution A and the solution B are simultaneously added, each through a constant flow control equipment, such as a peristaltic pump or a syringe pump, to the reactor.

Embodiment 7. The method of any one of embodiments 1 to 6, wherein the ratio of the flow rate of the solution A to the flow rate of the solution B ranges from about 1:10 to 1:1, including about 1:1, or from about 1:10 to less than 1:1, for example, from about 1:8 to 1:1.5, from about 1:6 to 1:2, or from about 1:4 to 1:3; and preferably about 1:3 to 1:1.

Embodiment 8. The method of embodiment 7, wherein the ratio of the flow rate of the solution A to the flow rate of the solution B is about 1:2 or 1:3.

Embodiment 9. The method of embodiment 7, wherein the ratio of the flow rate of the solution A to the flow rate of the solution B is about 1:1.

Embodiment 10. The method of any one of embodiments 1 to 9, wherein the flow rate of the solution A and the flow rate of the solution B are each not more than about 1000 mL/min, for example, not more than about 900 mL/min, about 800 mL/min, about 700 mL/min, about 600 mL/min, about 500 mL/min, about 400 mL/min, about 300 mL/min, about 200 mL/min, or about 100 mL/min, or not more than about 90 mL/min, about 80 mL/min, about 60 mL/min, about 50 mL/min, or about 30 mL/min, for example, not more than about 25 mL/min, or not more than about 20 mL/min, for example, from about 2 to 30 mL/min, from about 4 to 25 mL/min, from about 8 to 20 mL/min, or from about 10 to 15 mL/min.

Embodiment 11. The method of any one of embodiments 1 to 10, wherein the flow rate of the solution A and the flow rate of the solution B are each not more than about 15 mL/min.

Embodiment 12. The method of any one of embodiments 1 to 11, wherein the flow rate of the solution A and the flow rate of the solution B each range from about 2 to 15 mL/min, for example, from about 3 to 12 mL/min, or from about 6 to 10 mL/min.

Embodiment 13. The method of any one of embodiments 1 to 12, wherein the flow rate of the solution A is from about 2 to 10 mL/min, such as about 2, 3, 4, 5, 6, 7, 8, 9 or 10 mL/min.

Embodiment 14. The method of any one of embodiments 1 to 13, wherein the flow rate of the solution B is from about 2 to 15 mL/min, such as about 2, 3, 4, 6, 8, 12, 14 or 15 mL/min.

Embodiment 14-A. The method of any one of embodiments 1 to 14, wherein the molar ratio of the base to the 5-aminouracil of Formula (II') ranges from about 3.0:1.0 to about 6.0:1.0;

preferably, the molar ratio of the base to the compound of Formula (II') ranges from about 3.0:1.0 to about 5.5:1.0.

Embodiment 14-B. The method of any one of embodiments 1 to 14 and embodiment 14-A, wherein the molar ratio of the oxidant to the 5-aminouracil of Formula (II') ranges from about 3.0:1.0 to about 3.5:1.0;

preferably, the molar ratio of the metal oxidant to the compound of Formula (II') is from about 3.0:1.0 to about 3.4:1.0.

Embodiment 15. The method of any one of embodiments 1 to 14 and embodiments 14-A and 14-B, wherein the solvent in the solution A and the solvent in the solution B are each a polar solvent.

Embodiment 16. The method of embodiment 15, wherein the polar solvent is one, two or more selected from the group consisting of water, methanol, ethanol, acetonitrile and tetrahydrofuran, and preferably water.

Embodiment 17. The method of any one of embodiments 1 to 16, wherein the solution A and the solution B each have a temperature ranging from about 0 to 8° C., for example, from about 0 to 4° C., or from about 2 to 6° C.

Embodiment 18. The method of any one of embodiments 1 to 17, wherein the reaction in step S2 is conducted at a temperature of from about −20 to 20° C., preferably from about −10 to 10° C., for example, from about −5 to 5° C., such as about −10, −5, 0 or 5° C.

Embodiment 19. The method of any one of embodiments 1 to 18, wherein the oxidant is used in about 3 to 5 equivalents, relative to the 5-aminouracil of Formula (II').

Embodiment 20. The method of any one of embodiments 1 to 19, wherein the oxidant is a reagent comprising Fe(III) or Mn(III).

Embodiment 21. The method of embodiment 20, wherein the oxidant is one or more selected from the group consisting of potassium ferricyanide, sodium pentacyano-monocarbonylferroate ($Na_2[Fe(CN)_5(CO)]$), sodium pentacyanoammineferroate ($Na_3[Fe(CN)_5NH_3]$), lithium ferricyanide, sodium ferricyanide, ferric chloride, ferric bromide, manganese (III) acetylacetonate and manganese (III) acetate, preferably potassium ferricyanide.

Embodiment 22. The method of any one of embodiments 1 to 21, wherein the base in step S2 is one or more selected from the group consisting of sodium hydroxide, sodium bicarbonate, sodium carbonate, potassium hydroxide, potassium bicarbonate, potassium carbonate, lithium hydroxide, aqueous ammonia, $Li_2CO_3$, $Rb_2CO_3$, RbOH, $Cs_2CO_3$, CsOH, $BeCO_3$, $Be(OH)_2$, $MgCO_3$, $Mg(OH)_2$, $CaCO_3$, $Ca(OH)_2$, $SrCO_3$, $Sr(OH)_2$, $BaCO_3$ and $Ba(OH)_2$, preferably potassium hydroxide.

Embodiment 23. The method of any one of embodiments 1 to 22, wherein the base is used in about 3 to 5 equivalents, relative to the 5-aminouracil of Formula (II').

Embodiment 24. The method of any one of embodiments 1 to 23, wherein the reaction in step S2 is conducted for a period of from about 10 seconds to 10 minutes or more, for example, from about 20 seconds to 8 minutes, from about 30 seconds to 6 minutes, from about 40 seconds to 5 minutes, or from about 50 seconds to 4 minutes.

Embodiment 25. The method of any one of embodiments 1 to 24, wherein the reactor is a microreactor, such as a microchannel reactor or a micromixer.

Embodiment 26. The method of any one of embodiments 1 to 25, wherein the method comprises the step of:

(S2) simultaneously adding a solution of 5-aminouracil of Formula (II') and sodium hydroxide or potassium hydroxide, preferably potassium hydroxide, in water at about 0 to 4° C. and an aqueous solution of potassium ferricyanide at about 0 to 4° C. at the same constant flow rate to a microreactor for mixing, and reacting at a temperature ranging from about −5 to 5° C. to obtain pyrimido[4, 5-g]pteridine-2,4,7,9 (1H,3H,6H,8H)-tetraone of Formula (I'), wherein the constant flow rate preferably ranges from about 3 to 10 mL/min.

Embodiment 27. The method of any one of embodiments 1 to 24, wherein the reactor is an ordinary reactor, such as a tubular reactor or a tank reactor.

Embodiment 28. The method of embodiment 27, wherein the reactor has been pre-cooled to a temperature ranging from about 0° C. to −20° C., for example, from about −5° C. to −15° C., or from about −10° C. to −15° C.

Embodiment 29. The method of embodiment 27 or 28, wherein the solution A and the solution B are mixed by stirring at a speed ranging from about 100 to 1000 rpm (for example, from about 200 to 900 rpm, from about 300 to 800 rpm, from about 400 to 700 rpm, or from about 500 to 600 rpm).

Embodiment 30. The method of any one of embodiments 27 to 29, wherein the method comprises the step of:

(S2) under stirring at a speed ranging from about 200 to 600 rpm (for example, from about 300 to 500 rpm), simultaneously adding a solution of 5-aminouracil of Formula (II') and sodium hydroxide or potassium hydroxide, preferably potassium hydroxide, in water at about 0 to 4° C. and an aqueous solution of potassium ferricyanide at about 0 to 4° C., each at a constant flow rate, to the reactor precooled to a temperature of from about 0° C. to about −20° C., for example, at about −10° C., for mixing, to obtain pyrimido[4,5-g]pteridine-2,4,7,9(1H,3H,6H,8H)-tetraone of Formula (I'), wherein the flow rate ratio of the solution of 5-aminouracil to the solution of potassium ferricyanide is about 1:2.

Embodiment 31. A method for preparing 3,6-diaminopyrazine-2,5-dicarboxylic acid of Formula 4, comprising the steps of:

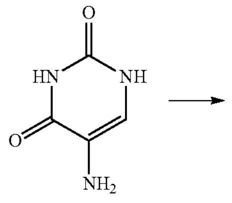

II'

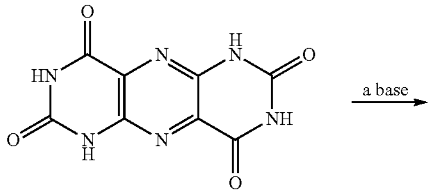

I'

-continued

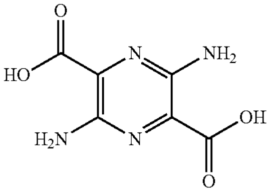

4

(S2') preparing pyrimido[4,5-g]pteridine-2,4,7,9(1H,3H, 6H,8H)-tetraone of Formula (I') from 5-aminouracil of Formula (II') by the method of any one of embodiments 1 to 30; and (S3) hydrolyzing the pyrimido[4,5-g]pteridine-2,4,7,9 (1H,3H,6H,8H)-tetraone of Formula (I') in the presence of a base to obtain 3,6-diaminopyrazine-2,5-dicarboxylic acid of Formula 4.

Embodiment 32. The method of embodiment 31, wherein the hydrolysis in step S3 is conducted in a polar solvent.

Embodiment 33. The method of embodiment 32, wherein the polar solvent is one or more selected from the group consisting of water, methanol, ethanol, acetonitrile, tetrahydrofuran, diethylene glycol dimethyl ether and methyl isobutyl ketone, and preferably water.

Embodiment 34. The method of any one of embodiments 31 to 32, the base in step S3 is one or more selected from the group consisting of sodium hydroxide, sodium bicarbonate, sodium carbonate, potassium hydroxide, potassium bicarbonate, potassium carbonate and lithium hydroxide, and preferably sodium hydroxide.

Embodiment 35. The method of any one of embodiments 31 to 34, wherein the hydrolysis in step S3 is conducted at a temperature ranging from about 150 to 200° C., and preferably from about 170 to 180° C.

Embodiment 36. The method of any one of embodiments 31 to 35, wherein the hydrolysis is conducted for about 4 to 8 hours.

Embodiment 37. The method of any one of embodiments 1 to 36, wherein the method may further comprise the step of:

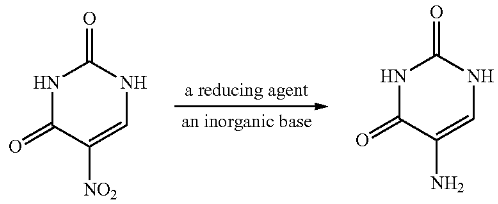

III II'

(S1) reacting 5-nitrouracil of Formula (III) with a reducing agent in the presence of an inorganic base to obtain 5-aminouracil of Formula (II'), wherein the inorganic base is not ammonia.

Embodiment 38. A method for preparing 5-aminouracil of Formula (II'), wherein the method comprises the step of:

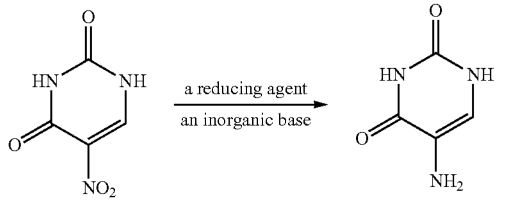

III II'

(S1) reacting 5-nitrouracil of Formula (III) with a reducing agent in the presence of an inorganic base to obtain 5-aminouracil of Formula (II'), wherein the inorganic base is not ammonia.

Embodiment 39. The method of embodiment 37 or 38, wherein in step S1, the reducing agent is used in about 1 to 6 equivalents, preferably about 4 to 6 equivalents, relative to 5-nitrouracil of Formula (III).

Embodiment 40. The method of any one of embodiments 37 to 39, wherein the inorganic base is one or more selected from the group consisting of sodium hydroxide, potassium hydroxide, lithium hydroxide, sodium carbonate, potassium carbonate, sodium bicarbonate and potassium bicarbonate, and preferably sodium bicarbonate.

Embodiment 41. The method of any one of embodiments 37 to 40, wherein in step S1, the inorganic base is used in about 4 to 6 equivalents, relative to 5-nitrouracil of Formula (III).

Embodiment 42. The method of any one of embodiments 37 to 41, wherein the reducing agent is one or more selected from the group consisting of $Na_2S_2O_4$, hydrogen, iron powder and zinc powder, and preferably $Na_2S_2O_4$.

Embodiment 43. The method of any one of embodiments 37 to 42, wherein the reaction temperature in step S1 ranges from about 60 to 90° C., preferably from about to 85° C., more preferably from about 75 to 85° C., for example, from about 75 to or from about 80 to 85° C.

Embodiment 44. The method of any one of embodiments 37 to 43, wherein the reaction time in step S1 is from about 1 to 10 hours, for example, from about 2 to 8 hours, preferably from about 3 to 6 hours, such as about 3, 4, 5 or 6 hours.

Beneficial Effects

With respect to the method according to the second, third and fourth aspects of the present disclosure, firstly the production process becomes safer and more environmentally friendly by changing the inorganic base in step S1 to avoid the use of aqueous ammonia in the present invention. Unexpectedly, it has also been found that the yield of the modified step S1 is greatly improved, which can be up to 92% (see Example 11), as compared to the reduction reaction of Synthetic route 2 (yield: 65%, see Comparative Example 1).

In addition, by improving the step S2, by simultaneously adding the solution containing 5-aminouracil of formula (II') and the solution containing the oxidant, each at an appropriate constant flow rate, to the reactor for mixing, the yield of the reaction is dramatically increased, for example, from 20% of Synthetic route 2 (see Comparative Example 1) to 84% (see Example 11), thereby successfully eliminating the limitations on the overall yield in Synthetic route 2. The steps S1, S2 (or S2') and S3 of the present disclosure have an overall yield that can reach 60% or higher (the overall yield in Example 11 is about 62%), and thereby greatly reduce the production cost, improve the production operability and economic benefits, and are more conducive to industrial production. In addition, through the improvement of step S2, the method of the present disclosure has the potential to reduce the emission of small molecules, such as urea as a by-product.

Specific Mode for Carrying Out the Invention

The invention will be described in further detail below with reference to specific examples. The following examples are only for understanding the method and core idea of the present invention, and are not intended to limit the scope of the present invention. It will be apparent to those skilled in the art that any possible modifications or substitutions without departing from the spirit of the invention are within the scope of the invention.

Experimental methods for which specific conditions are not specified in the examples are usually under conventional conditions, or conditions as recommended by the manufacturer of the raw material or commodity; reagents without source indication are generally conventional reagents that are commercially available or can be prepared from known reagents by conventional methods.

EXAMPLES

Example 1: Preparation of Pteridine from the Monopotassium Salt of 5-aminouracil An aqueous solution of $K_3Fe(III)(CN)_6$ was prepared by dissolving $K_3Fe(III)(CN)_6$ (1.797 g, 5.46 mmol, 3.00 equiv.) in water (6.0 mL, deionized water (DI)). An aqueous solution of the monopotassium salt of 5-aminouracil was prepared by transferring 5-aminouracil (0.232 g, 1.83 mmol, 1.00 eq.) and water (1.0 mL, DI) into a centrifuge tube and slowly adding a solution of one equivalent of KOH (0.120 g, 1.82 mmol, 1.00 equiv. in 1.0 mL water DI) with vigorous mixing. A second KOH solution was prepared in a similar manner to the above preparation; KOH (0.356 g, mmol, 2.95 equiv.) was dissolved in water (2.0 mL, DI) in a reaction vessel. All solutions and the reaction vessel were cooled to 0° C. (NaCl/ice bath). All aqueous solutions were treated with nitrogen for several minutes. The potassium salt of solution and $K_3Fe(III)(CN)_6$ solution were transferred into separate syringes. Both syringes were positioned over the reaction vessel containing cold KOH solution (4.0 mL) maintained at 0° C. (NaCl/ice bath). The aqueous solutions of the potassium salt of 5-aminouracil and $K_3Fe(III)(CN)_6$ were simultaneously and rapidly injected at a rate of 5 to 10 mL/min into the KOH solution maintained at 0° C. (NaCl/ice bath). A red precipitate formed immediately. The reaction mixture was stirred rapidly and allowed to stand at 0° C. After several minutes, the red solid was separated from the reaction mixture. The remaining red solid was air dried and then dried over $P_2O_5$ and KOH. The isolated yield of the dipotassium salt of pyrimido[4,5-g]pteridine-2,4,7,9(1H,3H,6H,8H)-tetrone (pteridine) was 91%. The entire solid was then dissolved in water (10.0 mL, DI), diluted (100×) and quantified by rpHPLC (87%). According to rpHPLC (reverse phase HPLC, C18) analysis, the product is about 98% pure.

Faster addition rates of the aqueous solutions of the potassium salt of and $K_3Fe(III)(CN)_6$ are expected to work well. Slower addition rates are also effective.

Example 2: Preparation of Pteridine from the Monopotassium Salt of 5-aminouracil Pre-formed potassium salt of the 5-aminouracil (5-AU) was prepared by adding one equivalent of potassium hydroxide solution to a mixture of 5-aminouracil (2.0 g) in water (250 mL, DI) resulting in a slightly brown colored solution. The solution was frozen and lyophilized, producing a solid tan 5-AU potassium salt. This 5-AU potassium salt was used in place of the potassium salt formed as a two-step process as in Example 1 while all other conditions kept the same. The reaction using pre-formed potassium 5-AU salt gave an 83% yield of pteridine by HPLC quantitation.

Example 3: Preparation of Pteridine from the Monopotassium Salt of 5-aminouracil The conditions of Example 1 were used except KOH was replaced by $K_2CO_3$ (0.076 g, 0.55 mmol, 3.06 equiv.) dissolved in water (2.0 mL, DI). All other conditions were the same. The yield of pteridine was 88% by quantitative rpHPLC.

Example 4: Preparation of Pteridine from the Monopotassium Salt of 5-aminouracil The conditions of Example 1 were used except KOH was replaced by $NH_4OH$ in water (22%, 0.086 mL, 0.54 mol, 3.00 eq.) which was diluted to a 2.0 mL total volume with additional DI water. (0.076 g, 0.55 mmol, 3.06 equiv.). All other conditions were the same. The yield of pteridine was 88% by quantitative rpHPLC.

Example 5: Preparation of Pteridine from the Monopotassium Salt of 5-aminouracil The conditions of Example 1 were used except deionized water was replaced by potable (tap) water. No difference in yield could be elucidated in switching from deionized water to potable water.

Example 6: Preparation of Pteridine

An aqueous solution of $K_3Fe(III)(CN)_6$ was prepared by dissolving $K_3Fe(III)(CN)_6$ (0.907 g, 2.75 mmol, 3.02 equiv.) in water (6.0 mL, DI). An aqueous solution of the monopotassium salt of 5-aminouracil was prepared by adding dropwise a solution of KOH (0.206 g, 3.67 mmol, 4.02 equiv.) in 2.0 mL water DI) to (0.116 g, 0.91 mmol, 1.00 eq.) with vigorous mixing. The potassium KOH solution was transferred to a syringe and Fe(III) solution was transferred to a separate syringe. Both syringes were positioned over an empty reaction flask, and simultaneously both reagents were rapidly injected into the flask. A red precipitate formed immediately. The reaction mixture was rapidly stirred and allowed to stand at RT. After several minutes, the reaction tube was filtered. The remaining red solid was dissolved in water (10.0 mL, DI), diluted (100×) and quantified by rpHPLC (51%).

Example 7: Preparation of Pteridine

An aqueous solution of $K_3Fe(III)(CN)_6$ was prepared by dissolving $K_3Fe(III)(CN)_6$ (0.888 g, 2.70 mmol, 3.15 equiv.) in water (6.0 mL, DI). An aqueous solution of the monopotassium salt of 5-aminouracil was prepared by adding a solution of KOH (0.201 g, 3.58 mmol, 4.18 equiv.) in 1.0 mL water DI) into a flask containing 5-aminouracil (0.1 g, 0.86 mmol, 1.00 eq.) and water (1.0 mL, DI). All solutions in the reaction vessel were cooled to 0° C. in a NaCl/ice bath and then all solutions were simultaneously treated with helium for several minutes. The potassium solution/KOH was transferred to a syringe and Fe(III) solution was transferred to a separate syringe. Both syringes were positioned over an empty flask, and simultaneously added into the empty flask. A red precipitate formed immediately. The reaction mixture tube was rapidly stirred and allowed to stand at 0° C. After several minutes, the reaction tube filtered. The remaining red solid was dissolved in water (10.0 mL, DI), diluted (100×) and quantified by rpHPLC (54%).

Example 8: Scaled Preparation of Pteridine

An aqueous solution of $K_3Fe(III)(CN)_6$ was prepared by dissolving $K_3Fe(III)(CN)_6$ (0.902 g, 2.74 mmol, 3.03 equiv.) in water (3.0 mL, DI). An aqueous solution of the monopotassium salt of 5-aminouracil was prepared by dissolving (0.115 g, 0.90 mmol, 1.00 eq.) in water (0.5 mL, DI) and then slowly adding dropwise a solution of KOH (0.233 g, 3.53 mmol, 3.90 equiv. in 0.5 mL water, DI) with vigorous mixing. All aqueous solutions were cooled to 0° C. in a NaCl/ice bath and then were simultaneously treated with helium gas for several minutes. The Fe(III) solution was transferred to a syringe and rapidly injected into the potassium KOH solution over about 15 seconds. After several minutes, the reaction mixture was centrifuged and supernatant decanted. The remaining red solid was air dried and then dried over $P_2O_5$ and KOH. The isolated yield was 51%. The entire isolated red solid was then dissolved in water (10.0 mL, DI), diluted (100×) and quantified by rpHPLC (44%).

Example 9: Scaled Preparation of Pteridine

An aqueous solution of $K_3Fe(III)(CN)_6$ was prepared by dissolving $K_3Fe(III)(CN)_6$ (3.25 g, 9.9 mmol, 3.2 equiv.) in water (10.0 mL, DI). An aqueous solution of the monopotassium salt of 5-aminouracil was prepared by dissolving (0.394 g, 3.1 mmol, 1.0 equiv.) in water (5.0 mL, DI) and slowly adding dropwise a solution of KOH (0.200 g, 3.1 mmol, 1.0 equiv.) in water (5.0 mL, DI) into the 5-aminouracil solution with vigorous mixing. Another aqueous solution of KOH (0.614 g, 9.3 mmol, 3.0 equiv.) was prepared in water (13.5 mL, DI), and added to the bottom of a three-neck round-bottom flask. All solutions and the reaction vessel were cooled to 0° C. in a NaCl/ice bath, and then all solutions were simultaneously treated with nitrogen for several minutes. The reaction was carried out under nitrogen at 0° C. The solution of the potassium 5-aminouracil was transferred to a syringe, and Fe(III) solution was transferred to a separate syringe. Both syringes were pierced through the septum of the flask and simultaneously and rapidly injected into the flask containing the KOH solution. A red precipitate formed immediately. The reaction mixture in the flask was stirred vigorously for several minutes and allowed to stand at 0° C. The contents of the reaction mixture were transferred into a centrifuge tube and was washed with DI water, centrifuged, and supernatant decanted. The supernatant was analyzed by HPLC and shown to have only low concentration of the desired pteridine. The remaining red pteridine solid was air dried and then dried over $P_2O_5$ and KOH for several days until a consistent weight was obtained. This reaction was repeated twice as described above with an average isolated yield of pteridine of (47% for trial 1 and 44% for trial 2).

Example 10: Scaled Preparation of Pteridine

An aqueous solution of $K_3Fe(III)(CN)_6$ was prepared by dissolving $K_3Fe(III)(CN)_6$ (3.25 g, 9.9 mmol, 3.2 equiv.) in water (10.0 mL, DI). An aqueous solution of the monopotassium salt of 5-aminouracil was prepared by dissolving (0.394 g, 3.1 mmol, 1.0 equiv.) in water (5.0 mL, DI) and slowly adding dropwise an aqueous solution of KOH (0.200 g, 3.1 mmol, 1.0 equiv.) in water (5.0 mL, DI) with vigorous mixing. This solution of potassium salt of 5-aminouracil was then added to the bottom of a three-neck round-bottom flask. All solutions and the reaction vessel were cooled to 0° C. in a NaCl/ice bath, and all solutions were simultaneously treated with nitrogen for several minutes. The reaction was conducted under nitrogen at 0° C. The Fe(III) solution was transferred to a syringe. The syringe was pierced through the septum of the flask and rapidly injected into the flask containing the solution of the potassium salt of 5-aminouracil. A red precipitate (pteridine) formed almost immediately. The reaction mixture in the flask was stirred for several minutes and allowed to stand at 0° C. After several minutes, the product from the flask was washed into a centrifuge tube with DI water, centrifuged, and supernatant decanted. The remaining red solid was air dried and then dried over $P_2O_5$ and KOH for several days. The isolated yield of pteridine was 41%.

Example 11: Preparation of 3,6-diaminopyrazine-2,5-dicarboxylic acid

Step 1:

50 g of $Na_2S_2O_4$ was added in batches to a saturated aqueous solution of 10 g of and 20 g of sodium bicarbonate, and stirred at 75° C. for 4 hours. The resulting white precipitate was filtered, then washed with water and dried to give 7.4 g of 5-aminouracil (yield: 92%).

MS [M+H] 128.11.

Step 2:

A first solution was prepared by dissolving 70 g of 5-aminouracil and 93 g of potassium hydroxide in 1.4 L of water, and then cooled to 0° C. A second solution was prepared by dissolving 580 g of potassium ferricyanide in 1.4 L of water, and cooled to 0° C. The first and second solutions were simultaneously added to a mixing module of a microreactor by peristaltic pumps at the same flow rate of 10 mL/min, and maintained in the mixing module for 20 seconds to react at −5° C. The reaction mixture then passed from the outlet into a collection tank, and the resulting precipitate was filtered with suction and washed with 1 N hydrochloric acid and then dried to give 57.3 g of pyrimido[4,5-g]pteridine-2,4,7,9(1H,3H,6H,8H)-tetraone as a solid (purity: 99%, yield: 84%).

LC-MS [M−H] 247.02.

$^1$H NMR [500 MHz, DMSO-d6] 12.07 (br s, 2H), 11.79 (br s, 2H).

$^{13}$C NMR [500 MHz, DMSO-d6] 160.5, 150.0, 145.7, 130.1.

Step 3:

g of solid pyrimido[4,5-g]pteridine-2,4,7,9(1H,3H,6H,8H)-tetraone was added to 400 mL of water, followed by addition of aqueous sodium hydroxide (50 g, 500 mL). The resulting mixture was heated to 180° C. and reacted for 5 h, and a needle-like solid was precipitated. The reaction mixture was cooled and then filtered, and the resulting precipitate was filtered with suction and washed with 1 N hydrochloric acid, and dried to give 31.9 g of 3,6-diaminopyrazine-2,5-dicarboxylic acid as a solid (purity: 99%, yield: 80%).

MS [M−H] 197.02.

$^{13}$C NMR [500 MHz, DMSO-d6] 167.8, 148.5, 126.0.

Example 12: Preparation of 3,6-diaminopyrazine-2,5-dicarboxylic acid

Step 1:

50 g of $Na_2S_2O_4$ was added in batches to a saturated aqueous solution of 10 g of and 10 g of sodium hydroxide, and stirred at 85° C. for 3 hours. The resulting white precipitate was filtered and then dried to give 7.1 g of 5-aminouracil (yield: 88%). The characterization data for the resulting compound is the same as in Step 1 of Example 11.

Step 2:

A first solution was prepared by dissolving 30 g of 5-aminouracil and 50 g of sodium hydroxide in 500 mL of water, and cooled to 5° C. A second solution was prepared by dissolving 230 g of potassium ferricyanide in 1.4 L of water, and cooled to 2° C. The first and second solutions were simultaneously added to a mixing module of a microreactor by peristaltic pumps at flow rates of 2 mL/min and 6 mL/min, respectively, and maintained in the mixing module for 30 seconds to react at 0° C. The reaction mixture then passed from the outlet into a collection tank, and the resulting precipitate was filtered with suction and washed with 1 N hydrochloric acid and then dried to give 18.7 g of pyrimido[4,5-g]pteridine-2,4,7,9(1H,3H,6H,8H)-tetraone as a solid (purity: 99%, yield: 64%). The characterization data for the resulting compound is the same as in Step 2 of Example 11.

Step 3:

50 g of pyrimido[4,5-g]pteridine-2,4,7,9(1H,3H,6H,8H)-tetraone was added to 600 mL of pure water, followed by addition of aqueous potassium hydroxide (70 g, 500 mL). The resulting mixture was heated to 180° C. and reacted with stirring for 8 hours. The reaction solution was acidified with 1 N hydrochloric acid and then filtered, and the resulting precipitate was slurried and dried to give 29.9 g of 3,6-diaminopyrazine-2,5-dicarboxylic acid (purity: 99%, yield: 75%). The characterization data for the resulting compound is the same as in Step 3 of Example 11.

Example 13: Preparation of 3,6-diaminopyrazine-2,5-dicarboxylic acid

Step 1:

50 g of $Na_2S_2O_4$ was added in batches to a saturated aqueous solution of 10 g of and 19 g of sodium carbonate and stirred at 60° C. for 6 hours. The resulting white precipitate was filtered and then dried to give 6.9 g of 5-aminouracil (yield: 85%). The characterization data for the resulting compound is the same as in Step 1 of Example 11.

Step 2:

A first solution was prepared by dissolving 70 g of 5-aminouracil and 93 g of potassium hydroxide in 1.4 L of water, and cooled to 0° C. A second solution was prepared by dissolving 600 g of potassium ferricyanide in 1.4 L of water, and cooled to 0° C. The first and second solutions were simultaneously added to a mixing module of a microreactor by peristaltic pumps at the same flow rate of 3 mL/min to react, and maintained in the mixing module for 280 seconds to react at 5° C. The reaction mixture then passed from the outlet into a collection tank, and the resulting precipitate was filtered with suction and washed with 1 N hydrochloric acid and then dried to give 54.5 g of pyrimido[4,5-g]pteridine-2,4,7,9(1H,3H,6H,8H)-tetraone as a solid (purity: 99%, yield: 79%). The characterization data for the resulting compound is the same as in Step 2 of Example 11.

Step 3:

50 g of pyrimido[4,5-g]pteridine-2,4,7,9(1H,3H,6H,8H)-tetraone was added to 400 mL of water, followed by addition of aqueous potassium hydroxide (70 g, 600 mL). The resulting mixture was heated to 170° C. and reacted with stirring for 4 hours. The reaction solution was acidified with 1 N hydrochloric acid and then filtered, and the resulting precipitate was slurried and dried to give 31.1 g of 3,6-diaminopyrazine-2,5-dicarboxylic acid (purity: 99%, yield: 78%). The characterization data for the resulting compound is the same as in Step 3 of Example 11.

Example 14: Preparation of 3,6-diaminopyrazine-2,5-dicarboxylic acid

A first solution was prepared by dissolving 127 g of 5-aminouracil and 224 g of potassium hydroxide in 1.4 L of water, and cooled to 4° C. A second solution was prepared by dissolving 1060 g of potassium ferricyanide in 2.8 L of water, and cooled to 4° C. The first and second solutions were simultaneously added to a reaction kettle precooled to −10° C. by peristaltic pumps at constant flow rates of 7 mL/min and 14 mL/min, respectively. The mixed solutions were stirred at 300 rpm. After the reaction solutions were mixed, they were allowed to slowly return to room temperature. The reaction mixture was then filtered with suction, and the resulting filter cake was acidified with 1N hydrochloric acid, then filtered, washed and dried to give 104 g of pyrimido[4,5-g]pteridine-2,4,7,9(1H,3H,6H,8H)-tetraone as a solid (purity: 99%, yield: 84%). The characterization data for the resulting compound is the same as in Step 2 of Example 11.

g of pyrimido[4,5-g]pteridine-2,4,7,9(1H,3H,6H,8H)-tetraone was added to 1000 mL of water, and then potassium hydroxide (105 g) was added and mixed. The resulting mixture was heated to 180° C. and reacted with stirring for 6 hours. The reaction solution was acidified with 1 N hydrochloric acid and then filtered, and the resulting solid was slurried and filtered, and the filter cake was dried to give 48 g of 3,6-diaminopyrazine-2,5-dicarboxylic acid (purity: 99%, yield: 75%). The characterization data for the resulting compound is the same as in Step 3 of Example 11.

Comparative Example 1: Preparation of pyrimido[4,5-g]pteridine-2,4,7,9 (1H,3H,6H,8H)-tetraone and 3,6-diaminopyrazine-2,5-dicarboxylic acid The preparation of the compounds of formula (I') was conducted with reference to DE 10 2016 205 615 A1.

Step 1:

50 g of $Na_2S_2O_4$ was added in batches to an aqueous solution of 10 g of and 35 mL of aqueous ammonia (25%) and stirred at 75° C. for 4 hours. The resulting white precipitate was filtered and then dried to give 5.3 g of (yield: 65%). The characterization data for the resulting compound is the same as in Step 1 of Example 11.

Step 2:

70 g of 5-aminouracil and 93 g of potassium hydroxide were dissolved in 1.4 L of water. The resulting aqueous solution was cooled to 0° C., and a solution of potassium ferricyanide (600 g) in water (1.4 L) was slowly added dropwise thereto over a period of about 2 hours. The reaction mixture was then stirred for additional one hour, the resulting precipitate was then filtered with suction, washed with 1 N hydrochloric acid and dried to give 13.7 g of pyrimido[4,5-g]pteridine-2,4,7,9(1H, 3H,6H,8H)-tetraone as a solid (purity: 97%, yield: 20%). The yield of pyrimido[4,5-g]pteridine-2,4,7,9(1H,3H,6H,8H)-tetraone reported in DE 10 2016 205 615 A1 was 21% (see paragraph [0095]), which is similar to the yield here. The characterization data for the resulting compound is the same as in Step 2 of Example 11.

Step 3:

50 g of pyrimido[4,5-g]pteridine-2,4,7,9(1H,3H,6H,8H)-tetraone was added to 800 mL of water followed by addition of aqueous sodium hydroxide (70 g, 500 mL). The resulting mixture was heated to 170° C. and reacted with stirring for 5 hours. The reaction solution was acidified with 1 N hydrochloric acid and then filtered, and the resulting precipitate was slurried and dried to give 29.9 g of 3,6-diaminopyrazine-2,5-dicarboxylic acid (purity: 98%, yield: 75%). The characterization data for the resulting compound is the same as in Step 3 of Example 11.

Comparative Example 2: Preparation of pyrimido[4,5-g]pteridine-2,4,7,9 (1H,3H,6H,8H)-tetraone and 3,6-diaminopyrazine-2,5-dicarboxylic acid The preparation of the compound of formula (I') was conducted with reference to DE 10 2016 205 615 A1, except that only the order of addition in step 2 was adjusted.

Step 1:

50 g of $Na_2S_2O_4$ were added in batches to an aqueous solution of 10 g of and 35 mL of aqueous ammonia (25%) and stirred at 75° C. for 4 hours. The resulting white precipitate was filtered and then dried to give 5.3 g of (yield: 65%). The characterization data for the resulting compound is the same as in Step 1 of Example 11.

Step 2:

70 g of 5-aminouracil and 93 g of potassium hydroxide were dissolved in 1.4 L of water. The resulting aqueous solution was cooled to 0° C., and the above solution was slowly added dropwise to a solution of potassium ferricyanide (600 g) in water (1.4 L) over a period of about 2 hours. The reaction mixture was then stirred for additional one hour, the resulting precipitate was then filtered with suction, washed with 1 N hydrochloric acid and dried to give 24 g of pyrimido[4,5-g]pteridine-2,4,7,9(1H,3H,6H,8H)-tetraone as a solid (purity: 97%, yield: 35%). The yield of pyrimido[4,5-g]pteridine-2,4,7,9(1H,3H,6H,8H)-tetraone reported in DE 10 2016 205 615 Al is 21% (see paragraph [0095]). The characterization data for the resulting compound is the same as in Step 2 of Example 11.

Step 3:

50 g of pyrimido[4,5-g]pteridine-2,4,7,9(1H,3H,6H,8H)-tetraone was added to 800 mL of water, followed by addition of aqueous sodium hydroxide (70 g, 500 mL). The resulting mixture was heated to 170° C. and reacted with stirring for 5 hours. The reaction solution was acidified with 1 N hydrochloric acid and then filtered, and the resulting precipitate was slurried and dried to give 29.9 g of 3,6-diaminopyrazine-2,5-dicarboxylic acid (purity: 98%, yield: 75%). The characterization data for the resulting compound is the same as in Step 3 of Example 11.

Each reference cited in this application, including all patents, patent applications, journal articles, books, and any other publications, is incorporated herein by reference in its entirety.

What is claimed is:

1. A method for preparing a compound of Formula (I) or a salt thereof, the method comprising:

Formula (I)

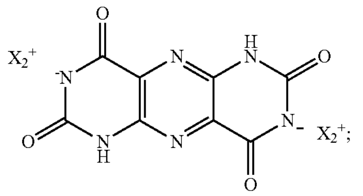

simultaneously contacting an aqueous solution of a compound of Formula (II) or a salt thereof:

Formula (II)

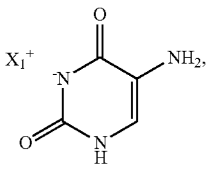

and an aqueous solution comprising a metal oxidant, each added at a constant flow rate through constant flow control equipment, into a vessel that contains an aqueous solution comprising a proton acceptor to form a reactant solution, and mixing the reactant solution to form the compound of Formula (I) or a salt thereof; or simultaneously adding the aqueous solution of the compound of formula (II) or the salt thereof containing the proton acceptor and the aqueous solution of a metal oxidant at a constant rate respectively to the vessel to form the reactant solution, and mixing the reactant solution to form the compound of Formula (I) or a salt thereof;

wherein $X_1^+$and $X_2^+$are each independently selected from the group consisting of $H^+$, $Li^+$, $Na^+$, $K^+$, $Rb^+$, $Cs^+$, $NH_4^+$, $Be^{2+}$, $Mg^{2+}$, $Ca^{2+}$, $Sr^{2+}$, and $Ba^{2+}$;

wherein the constant rate of the aqueous solution of the compound of formula (II) or a salt thereof and the constant rate of the aqueous solution of the metal oxidant may be same or different;

wherein the compound of Formula (I) or a salt thereof is formed within seconds of the simultaneous contacting of the aqueous solutions;

and wherein yield of the compound of Formula (I) or a salt thereof is at least 80%.

2. The method of claim 1, wherein $X_1^+$and $X_2^+$are independently selected from the group consisting of Na, $K^+$, and $NH_4^+$.

3. The method of claim 1, wherein the proton acceptor is selected from the group consisting of $Li_2CO_3$, LiOH, $Na_2CO_3$, NaOH, $K_2CO_3$, KOH, $Rb_2CO_3$, RbOH, $Cs_2CO_3$, CsOH, $NH_4OH$, $BeCO_3$, $Be(OH)_2$, $MgCO_3$, $Mg(OH)_2$, $CaCO_3$, $Ca(OH)_2$, $SrCO_3$, $Sr(OH)_2$, $BaCO_3$ and $Ba(OH)_2$.

4. The method of claim 1, wherein a molar ratio of the proton acceptor to the compound of Formula (II) ranges from about 3.5:1.0 to about 6.0:1.0.

5. The method of claim 1, wherein the metal oxidant is selected from the group consisting of potassium ferricyanide, lithium ferricyanide, sodium ferricynide, ferric chloride, ferric bromide, manganese (III) acetylacetonate, manganese (III) acetate, sodium pentacyanomonocarbonylferroate ($Na_2[Fe(CN)_5\ (CO)]$) and sodium pentacyanoammineferroate ($Na_3[Fe(CN)_5NH_3]$).

6. The method of claim 1, wherein a molar ratio of the metal oxidant to the compound of Formula (II) ranges from about 2.8:1.0 to about 3.5:1.0.

7. The method of claim 1, wherein the method is conducted at a temperature ranging from about −6° C. to about 25° C.

8. The method of claim 1, wherein the proton acceptor is selected from the group consisting of $Li_2CO_3$, LiOH, $Na_2CO_3$, NaOH, $K_2CO_3$, KOH, $Rb_2CO_3$, RbOH, $Cs_2CO_3$, CsOH, $NH_4OH$, $BeCO_3$, $Be(OH)_2$, $MgCO_3$, $Mg(OH)_2$, $CaCO_3$, $Ca(OH)_2$, $SrCO_3$, $Sr(OH)_2$, $BaCO_3$ and $Ba(OH)_2$; the metal oxidant comprises Fe(III) or Mn(III); a molar ratio of the proton acceptor to the compound of Formula (II) ranges from about 3.5:1.0 to about 6.0:1.0; the molar ratio of the metal oxidant to the compound of Formula (II) ranges from about 2.8:1.0 to about 3.5:1.0; and the method is conducted at a temperature ranging from about −6°° C. to about 25° C.

9. The method of claim 1, wherein the proton acceptor is selected from the group consisting of $Na_2CO_3$, NaOH, $K_2CO_3$, KOH, and $NH_4OH$; the metal oxidant is selected from potassium ferricyanide, lithium ferricyanide, sodium ferricynide, ferric chloride, ferric bromide, manganese (III) acetylacetonate or manganese (III) acetate; a molar ratio of the proton acceptor to the compound of Formula (II) ranges from about 3.5:1.0 to about 6.0:1.0; the molar ratio of the metal oxidant to the compound of Formula (II) ranges from about 2.8:1.0 to about 3.5:1.0; and the method is conducted at a temperature ranging from about −6° C. to about 25° C.

10. The method of claim 1, wherein the proton acceptor is KOH; the metal oxidant is potassium ferricyanide; a molar ratio of KOH to the compound of Formula (II) ranges from about 3.5:1.0 to about 6.0:1.0; the molar ratio of potassium ferricyanide to the compound of Formula (II) ranges from about 2.8:1.0 to about 3.5:1.0; and the method is conducted at a temperature ranging from about −6°° C. to about 25° C.

11. The method of claim 1, wherein the compound of Formula (I) is formed within seconds of the simultaneous contacting of the aqueous solutions of the compound of Formula (II), the proton acceptor, and the metal oxidant.

12. The method of claim 1, wherein the compound of Formula (I) has a percent yield of at least 90%.

13. The method of claim 1, wherein the compound of Formula (I) has a purity of greater than about 98%.

14. The method of claim 1, wherein the aqueous solution of the compound of Formula (II) and the aqueous solution of the metal oxidant are simultaneously added to the vessel each at a constant rate, and mixed, and wherein the constant rate of the compound of Formula (II) and the constant rate of the metal oxidant may be the same or different.

15. The method of claim 1, wherein a ratio of the rate of the aqueous solution of the compound of Formula (II) to the rate of the aqueous solution of the metal oxidant ranges from about 1:10 to 1:1.

16. The method of claim 1, wherein the constant flow control equipment comprises a peristaltic pump or a syringe pump.

17. The method of claim 1, wherein the rate of the aqueous solution of the compound of Formula (II) and the rate of the aqueous solution of the metal oxidant are each not more than about 1000 mL/min.

18. The method of claim 1, wherein the proton acceptor and the compound of Formula (II) are comprised together in an aqueous solution.

19. The method of 1, wherein the vessel is a microreactor or an ordinary reactor.

20. A method for preparing pyrimido [4,5-g]pteridine -2,4,7,9(1H,3H,6H,8H)-tetraone of Formula (I'), wherein the method comprises:

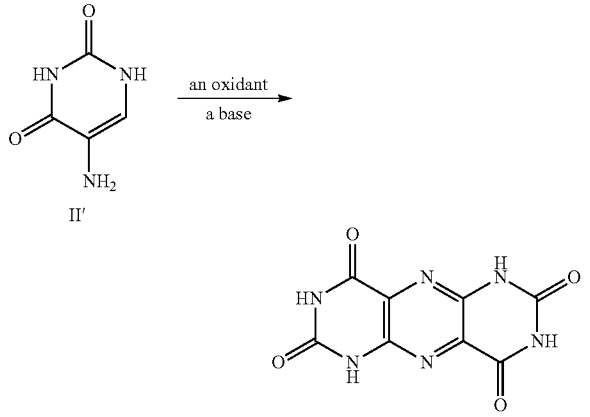

II'

I'

(S2) reacting 5-aminouracil of Formula (II') in the form of a solution A with an oxidant in the form of a solution B in the presence of a base in a reactor to obtain pyrimido [4,5-g] pteridine -2,4,7,9 (1H,3H,6H,8H)-tetraone of Formula (I'), wherein the solution A and the solution B are simultaneously added each at a constant flow rate to the reactor, and mixed, and wherein the constant flow rate of the solution A and the constant flow rate of the solution B may be the same or different;

wherein reaction is complete within seconds of the addition; and wherein yield of Formula (I') is at least 80%.

21. The method of claim 20, wherein the base and the 5-aminouracil are comprised together in the solution A.

22. The method of claim 20, wherein the solution A and the solution B are simultaneously added, each through a constant flow control equipment to the reactor.

23. The method of claim 20, wherein a ratio of the flow rate of the solution A to the flow rate of the solution B ranges from about 1:10 to 1:1.

24. The method of claim 20, wherein the flow rate of the solution A and the flow rate of the solution B are each not more than about 1000 mL/min.

25. The method of claim 20, wherein the flow rate of the solution A and the flow rate of the solution B are each not more than about 15 mL/min.

26. The method of claim 20, wherein a molar ratio of the base to the 5-aminouracil of Formula (II') ranges from about 3.0:1.0 to about 6.0:1.0.

27. The method of claim 20, wherein a molar ratio of the oxidant to the 5-aminouracil of Formula (II') ranges from about 3.0:1.0 to about 3.5:1.0.

28. The method of claim 20, wherein:

the solvent in the solution A and the solvent in the solution B are each selected from the group consisting of water, methanol, ethanol, acetonitrile, tetrahydrofuran and any combination thereof; and/or the solution A and the solution B each have a temperature ranging from about 0 to 8° C.; and/or the reaction in step S2 is conducted at a temperature of from about −20 to 20° C.; and/or the oxidant is used in 3 to 5 equivalents relative to the 5-aminouracil of Formula (II'); and/or the oxidant is a reagent comprising iron(III) or Mn(III), preferably one or more selected from the group consisting of potassium ferricyanide, sodium pentacyanomonocarbonylferroate ($Na_2[Fe(CN)_5(CO)]$), sodium pentacyanoammineferroate ($Na_3[Fe(CN)_5NH_3]$), lithium ferricyanide, sodium ferricynide, ferric chloride, ferric bromide, manganese (III) acetylacetonate and manganese (III) acetate; and/or the base in step S2 is one or more selected from the group consisting of sodium hydroxide, sodium bicarbonate, sodium carbonate, potassium hydroxide, potassium bicarbonate, potassium carbonate, lithium hydroxide, aqueous ammonia, $Li_2CO_3$, $Rb_2CO_3$, RbOH, $Cs_2CO_3$, CsOH, $BeCO_3$, $Be(OH)_2$, $MgCO_3$, $Mg(OH)_2$, $CaCO_3$, $Ca(OH)_2$, $SrCO_3$, $Sr(OH)_2$, $BaCO_3$ and $Ba(OH)_2$.

29. The method of claim 20, wherein the reactor is a microreactor.

30. The method of claim 29, wherein the method comprises the step of:

(S2) simultaneously adding a solution of 5-aminouracil of Formula (II') and sodium hydroxide or potassium hydroxide, preferably potassium hydroxide, in water at about 0 to 4° C. and an aqueous solution of potassium ferricyanide at about 0 to 4° C. at the same constant flow rate to a microreactor for mixing, and reacting at a temperature ranging from about −5 to 5° C. to obtain pyrimido [4, 5-g] pteridine-2,4,7,9 (1H,3H,6H,8H)-tetraone of formula (I').

31. The method of claim 20, wherein the reactor is an ordinary reactor.

32. The method of claim 31, wherein the reactor has been pre-cooled to a temperature ranging from about 0° C. to −20° C.

33. The method of claim 31, wherein the solution A and the solution B are mixed by stirring at a speed ranging from about 100 to 1000 rpm.

34. The method of claim 31, wherein the method comprises the step of:

(S2) under stirring at a speed ranging from about 200 to 600 rpm, simultaneously adding a solution of 5-aminouracil of Formula (II') and sodium hydroxide or potassium hydroxide, in water at about 0 to 4° C. and an aqueous solution of potassium ferricyanide at about 0 to 4° C., each at a constant flow rate, to the reactor precooled to a temperature ranging from about 0° C. to about −20° C., for mixing, to obtain pyrimido [4,5-g] pteridine-2,4,7,9 (1H,3H,6H,8H)-tetraone of Formula (I'), wherein the flow rate ratio of the solution of 5-aminouracil to the solution of potassium ferricyanide is about 1:2.

35. A method for preparing 3,6-diaminopyrazine-2,5-dicarboxylic acid of Formula 4, wherein the method comprises the steps of:

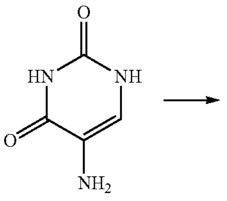

II'

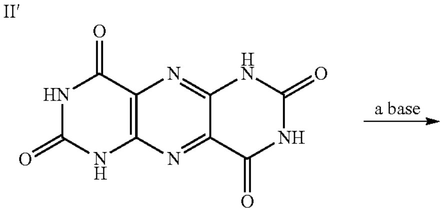

I'

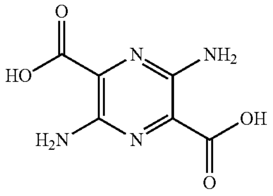

4

(S2') preparing pyrimido [4,5-g] pteridine-2,4,7,9 (1H, 3H,6H,8H)-tetraone of Formula (I') from 5-aminouracil of Formula (II') by the method of any one of claims 20 to 34; and (S3) hydrolyzing the pyrimido [4,5-g] pteridine-2,4,7,9 (1H,3H,6H,8H)-tetraone of Formula (I') in the presence of a base to obtain 3,6-diaminopyrazine-2,5-dicarboxylic acid of Formula 4.

36. The method of claim 35, wherein:

the hydrolysis in step S3 is conducted in a polar solvent, the polar solvent being one or more selected from the group consisting of water, methanol, ethanol, acetonitrile, tetrahydrofuran, diethylene glycol dimethyl ether, and methyl isobutyl ketone, and/or the base in step S3 is one or more selected from the group consisting of sodium hydroxide, sodium bicarbonate, sodium carbonate, potassium hydroxide, potassium bicarbonate, potassium carbonate and lithium hydroxide; and/or the hydrolysis in step S3 is conducted at a temperature ranging from about 150 to 200°° C.; and/or the hydrolysis in step S3 is conducted for about 4 to 8 hours.

37. The method of claim 20, wherein the method further comprises the step of:

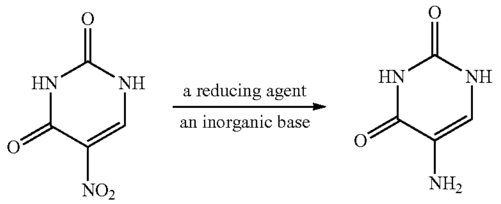

III II'

(S1) reacting 5-nitrouracil of Formula (III) with a reducing agent in the presence of an inorganic base to obtain 5-aminouracil of Formula (II'), wherein the inorganic base is not ammonia.

38. The method of claim 37, wherein:

the inorganic base is one or more selected from the group consisting of sodium hydroxide, potassium hydroxide, lithium hydroxide, sodium carbonate, potassium carbonate, sodium bicarbonate and potassium bicarbonate; and/or in step S1, the reducing agent is used in about 1 to 6 equivalents, preferably about 4 to 6 equivalents, relative to 5-nitrouracil of Formula (III); and/or the reducing agent is one or more selected from the group consisting of $Na_2S_2O_4$, hydrogen, iron powder, and zinc powder; and/or the reaction temperature in step S1 ranges from about 60 to 90° C.; and/or the reaction time in step S1 is from about 1 to 10 hours.

* * * * *